United States Patent
Ying

(10) Patent No.: US 10,902,647 B2
(45) Date of Patent: Jan. 26, 2021

(54) SYSTEM FOR ITERATIVELY RECONSTRUCTING COMPUTED TOMOGRAPHY IMAGES THROUGH THREE DOMAINS

(71) Applicant: Zhengrong Ying, Belmont, MA (US)

(72) Inventor: Zhengrong Ying, Belmont, MA (US)

( * ) Notice: Subject to any disclaimer, the term of this patent is extended or adjusted under 35 U.S.C. 154(b) by 62 days.

(21) Appl. No.: 16/270,692

(22) Filed: Feb. 8, 2019

(65) Prior Publication Data

US 2020/0258270 A1 Aug. 13, 2020

(51) Int. Cl.
*G06K 9/00* (2006.01)
*G06T 11/00* (2006.01)
*G01N 23/046* (2018.01)

(52) U.S. Cl.
CPC .......... *G06T 11/005* (2013.01); *G01N 23/046* (2013.01); *G01N 2223/401* (2013.01); *G06T 2210/41* (2013.01); *G06T 2211/424* (2013.01)

(58) Field of Classification Search
CPC ............... G06T 11/005; G06T 2210/41; G06T 2211/424; G01N 23/046; G01N 2223/401
See application file for complete search history.

(56) References Cited

U.S. PATENT DOCUMENTS

| | | | |
|---|---|---|---|
| 10,307,114 B1* | 6/2019 | Ray | A61B 6/5258 |
| 2008/0085040 A1* | 4/2008 | Basu | G06T 11/005 |
| | | | 382/128 |
| 2015/0243045 A1* | 8/2015 | Ra | A61B 6/032 |
| | | | 382/131 |
| 2016/0217596 A1* | 7/2016 | Koehler | G06T 11/006 |
| 2017/0178365 A1* | 6/2017 | Raupach | G06T 7/11 |
| 2018/0158216 A1* | 6/2018 | Cao | G01N 23/046 |
| 2020/0273215 A1* | 8/2020 | Wang | A61B 3/14 |

OTHER PUBLICATIONS

Jiang Hsieh, "Computed Tomography Principles, Design, Artifacts, and Recent Advances", 2nd Edition, ISBN: 978-0-470-56353-3, Nov. 2009.
A. C. Kak and Malcolm Slaney, "Principles of Computerized Tomographic Imaging", Society of Industrial and Applied Mathematics, ISBN: 978-0-898-71494-4, 2001.
Lucas L. Geyer, et. al., "State of the Art: Iterative CT Reconstruction Techniques", Radiology, Aug. 2015, vol. 276, No. 2, pp. 339-357.

* cited by examiner

*Primary Examiner* — Tom Y Lu

(57) ABSTRACT

A system for iteratively reconstructing computed tomography images through three domains is disclosed. The system comprises a raw domain processor, a projection domain processor, and an image domain processor. The system also comprises two iterative loops: one is through a raw synthesizer connecting the raw domain processor and the projection domain processor, and the other is through a projection synthesizer connecting the projection domain processor and the image domain processor respectively.

8 Claims, 2 Drawing Sheets

SYSTEM FOR ITERATIVELY RECONSTRUCTING COMPUTED TOMOGRAPHY IMAGES THROUGH THREE DOMAINS

RELATED APPLICATIONS

This patent application is related to the following pending U.S. applications and/or issued U.S. patents, the contents of which are incorporated herein in their entirety by reference:

"Configurable data measurement and acquisition systems for multi-slice X-ray computed tomography systems," invented by Zhengrong Ying, U.S. application Ser. No. 13/589,245, filed on Aug. 20, 2012, now U.S. Pat. No. 9,078,569, issued on Jul. 14, 2015.

"Adjustable photon detection systems for multi-slice X-ray computed tomography systems," invented by Zhengrong Ying, U.S. application Ser. No. 13/760,127, filed on Feb. 6, 2013, now U.S. Pat. No. 9,285,327, issued on Mar. 15, 2016.

"Anti-scatter collimators for detector systems of multi-slice X-ray computed tomography systems," invented by Zhengrong Ying, U.S. application Ser. No. 13/908,897, filed on Jun. 3, 2013, now U.S. Pat. No. 9,076,563, issued on Jul. 7, 2015.

"Apparatus for detecting X-rays," invented by Zhengrong Ying, U.S. application Ser. No. 14/700,178, filed on Apr. 30, 2015, now U.S. Pat. No. 9,835,733, issued on Dec. 5, 2017.

FIELD OF THE DISCLOSURE

The present disclosure relates to generating Computed Tomography (CT) images using detected X-rays signals, and more particularly to a system for iteratively reconstructing CT images through the following three domains: raw data domain, projection data domain, and image data domain.

BACKGROUND OF THE DISCLOSURE

In X-ray CT systems, X-rays are used to image internal structures and features of a region of a subject or an object. The terms "subject" and "object" shall include anything capable of being imaged. The imaging is performed by an X-ray CT system, which images internal structures and features of a plurality of thin planar slices or a 3D volume of a region of an object using X-rays. For medical applications, the imaging objects include human bodies.

An X-ray CT system generally comprises an X-ray source that provides a cone-shaped X-ray beam and an array of closely spaced X-ray detectors that face the X-ray source. The X-ray source and the array of detectors are mounted in a gantry so that a patient being imaged with the CT system, generally lying on an appropriate support couch, can be positioned within the gantry between the X-ray source and the array of detectors. The gantry and the couch are moveable relative to each other so that the X-ray source and the detector array can be positioned axially at desired locations along the patient's body.

The gantry comprises a stationary structure referred to as a stator and a rotary element referred to as a rotor, which is mounted to the stator so that the rotor is rotatable about the axial direction. In third generation CT systems, the X-ray source and the array of detectors are mounted on the rotor. Angular positions of the rotor about the axial direction are controllable so that the X-ray source can be positioned at desired angles, referred to as view angles, or view positions, or view indexes interchangeably, around a patient's body.

To image a slice in a region of a patient's body, the X-ray source is positioned at an axial position of the slice and the X-ray source is rotated around the slice to illuminate the slice with X-rays from a plurality of different view angles. At each view angle, detectors in the array of detectors generate signals responsive to the intensity of X-rays from the source that passes through the slice. The signals are processed to determine the amounts, by which X-rays from the X-ray source are attenuated over various path lengths through the slice that the X-rays traverse, in passing though the slice from the X-ray source to the detectors. The amounts, by which the X-rays are attenuated, are used to determine the X-ray absorption coefficients of materials in the slice as a function of position in the slice. The absorption coefficients are used to generate an image of the slice and to identify compositions and densities of tissues in the slice.

The X-ray detectors comprised in a detector array of CT system are generally packaged in a plurality of modules, hereinafter referred to as detector modules, each of which comprises a plurality of X-ray detector elements. Most modern CT systems are multi-slice CT systems designed to simultaneously image a plurality of slices of a patient. The X-ray detector elements in each detector module of a multi-slice CT scanner are arranged in a matrix of rows and columns. The X-ray detector matrices of any two CT detector modules in a CT system are substantially identical and comprise a same number of rows of detector elements and a same number of columns of detector elements. The modules are positioned one adjacent to and contiguous with the other in a closely packed array with their rows of detectors aligned end to end so that the X-ray detector elements form a plurality of long parallel rows of X-ray detector elements.

The signal detected and digitized by the X-ray detector system is used to reconstruct CT images to be evaluated by radiologists for diagnosis for medical applications. The CT image reconstruction typically uses filtered back projection (FBP) algorithms for fast computation. However, the underlying mathematical and physical model of the FBP algorithms is over-simplified and does not fully utilize the information obtained by a CT system.

SUMMARY OF THE DISCLOSURE

In one embodiment of the present disclosure, a system for iteratively reconstructing CT images is disclosed, comprising a CT data acquisition system for generating raw data for each detector element at each view, a raw domain processor for generating M sets of serial projection data for each detector at each view, where M is a predetermined number of bins of a discretized X-ray spectrum of the X-ray source corresponding to the CT data acquisition system, a projection domain processor for generating M sets of serial image data, an image domain processor for generating CT images, a raw synthesizer for generating synthesized raw data, and, a projection synthesizer for generating synthesized projection data.

In one embodiment of the present disclosure, the raw domain processor and the projection domain processor are connected through the raw synthesizer to form the first iteration loop to iteratively generate the serial projection data. Each of the M sets of serial projection data is a polynomial function of air corrected data with K serial coefficients, and K is the degree of the polynomial function. The serial coefficients are computed and updated iteratively by the raw domain processor through calculation of gradient terms.

In one embodiment of the present disclosure, the projection domain processor and the image domain processor are connected through the projection synthesizer to form the second iteration loop to iteratively generate the serial image data. Each of the M sets of serial image data is iteratively computed through a minimization of a cost function, consisting of a data fidelity term and a regularization term.

BRIEF DESCRIPTION OF THE DRAWINGS

The drawing figures depict embodiments by way of example, not by way of limitation. In the figures, like reference numerals refer to the same or similar elements.

DETAILED DESCRIPTION OF THE DRAWINGS

Figure 1:
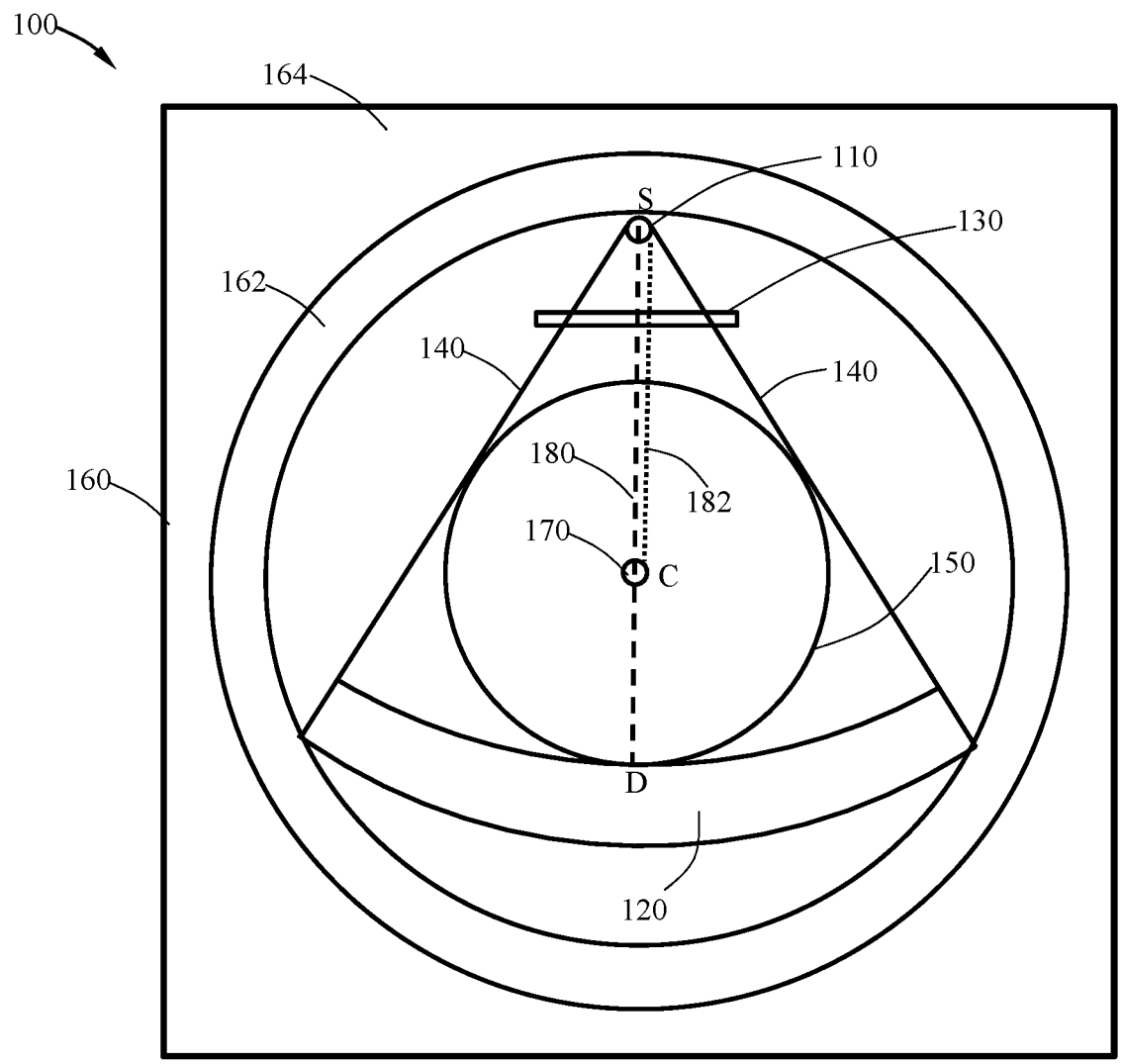
FIG. 1 illustrates a schematic functional diagram of a prior art multi-slice X-ray CT system.
Figure 1:
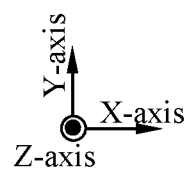

FIG. 1 shows a schematic functional diagram of a prior art multi-slice X-ray CT system 100. A multi-slice CT system typically comprises an X-ray source 110, which generates a cone-shaped X-ray beam 140. The X-ray beam 140 passes through a pre-patient collimator 130, which allows X-ray beam to illuminate only the targeted area and blocks X-ray beam in unwanted area. A patient usually lies down within the scanner's scanning Field Of View (FOV) 150, where the X-ray beam 140 illuminates. The X-ray detector system 120 receives X-ray photons and converts to analog signals that are proportional to X-ray photon energies. The X-ray CT system 100 also comprises a gantry 160, which includes a rotational part 162 and a stationary part 164. The X-ray source 110, the collimator 130 and the detector system 120 are mounted on the rotational part 162 of the gantry 160. The rotational part 162 rotates around the rotation center C 170.

The distance 182 between the focal spot S, which sometimes is interchangeably referred to as X-ray source position, of the X-ray source 110 and the rotation center C, which is interchangeably called iso-center, is hereinafter referred to as $R_{sc}$, and the distance 180 between the focal spot S of the X-ray source 110 and the detector system D is hereinafter referred to as focusing distance $R_{sd}$. Different CT systems may have different $R_{sc}$, $R_{sd}$, or/and scanning FOV.

The direction from the iso-center to the focal spot of the X-ray source is hereinafter referred to as Y-axis, and the direction perpendicular to the imaging plane or the rotation plane is hereinafter referred to as Z-axis, and the direction perpendicular to the Y-axis within the rotation plane is hereinafter referred to as X-axis.

Figure 2:
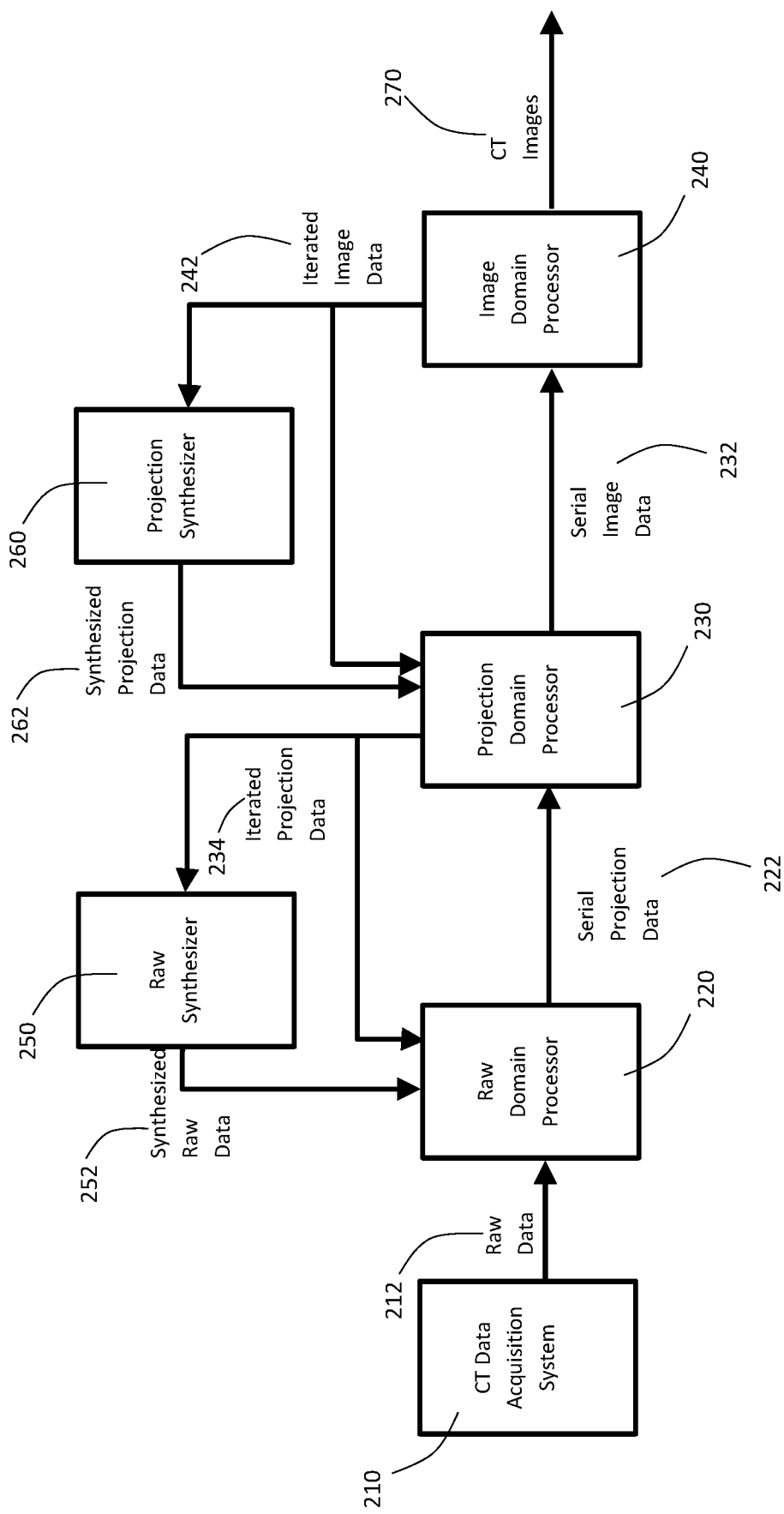
FIG. 2 illustrates an arrangement of a system for iteratively reconstructing CT images through three domains in accordance with one embodiment of the present disclosure.

FIG. 2 illustrates an arrangement of a system for iteratively reconstructing CT images through three domains in accordance with one embodiment of the present disclosure.

In accordance with one embodiment of the present disclosure, the CT Data Acquisition System (DAS) 210 in a CT detector system digitizes the analog signals generated from detectors to raw data 212, which is then fed to the raw domain processor 220 to generate the serial projection data 222, which is fed to the projection domain processor 230. The projection domain processor 230 generates the iterated projection data 234, which is fed to the raw synthesizer 250 and the raw domain processor 220. The projection domain processor 230 generates the serial image data 232, which is fed to the image domain processor 240 for processing. The image domain processor 240 generates the iterated image data 242, which is fed to the projection synthesizer 260 and the projection domain processor 230. The CT images 270 are also generated from image domain processor 240 to be used for example by radiologists for evaluation in medical applications.

The raw data R(n,c,v) is the signal received by each detector element (n, c) at each view v and digitized by the DAS 210 and contains the information of X-ray signal intensity attenuated by an object in the scanning field of view, where the detector row index n=0, . . . , N−1, the detector column index c=0, . . . , C−1, the view index v=0, . . . , V−1, and N, C, and V are the number of detector rows, the number of detector columns, and the number of views respectively. Each detector system comprises N rows and C columns of detector elements, totaling NC detector elements. The raw data comprises total NCV data points.

In accordance with one embodiment of the present disclosure, the raw domain processor 220 processes the raw data R(n,c,v) to generate the offset corrected data $R_o$(n,c,v) as follows, $$R_o(n,C,v)=R(n,C,v)-O(n,c,v) \qquad (1.1)$$

where the offset data O(n,c,v) is previously acquired and stored in the raw domain processor 220.

In accordance with one embodiment of the present disclosure, the raw domain processor 220 further processes the offset corrected data $R_o$(n,c,v) to generate air corrected data $P_a$(n,c,v) as follows, $$P_a(n,c,v)=A(n,c,v)-\ln R_o(n,c,v) \qquad (1.2)$$

where the air data A(n,c,v) is also previously acquired and stored in the raw domain processor 220.

In accordance with one embodiment of the present disclosure, the X-ray generated by the X-ray tube of the CT system contains a wide spectrum of energies denoted by S(E), where E=$E_0$, $E_0$+ΔE, . . . , $E_0$+(M−1)ΔE, corresponds to the discretized energy of the X-ray photons with each energy bin size of ΔE and total number of M bins, and $E_0$ is the first energy bin. The X-ray spectrum S(E) is previously obtained through simulation, experiments, or theoretically calculated, and is stored in the raw synthesizer 250, the raw domain processor 220, and the projection domain processor 230. The raw synthesizer 250 processes the iterated projection data 234, denoted as $P_i$(n,c,v), to generate the synthesized raw data $R_s$(n,c,v) as follows:

$$R_s(n, c, v) = \sum_E S(E) e^{-P_i(n,c,v,E)} \Delta E \qquad (1.3)$$

where $P_i$(n,c,v,E) is the iterated projection data 234 generated by the projection domain processor 230.

In accordance with one embodiment of the present disclosure, the raw domain processor 220 generates serial projection data 222 denoted as $P_s$(n,c,v,E), which is defined as a polynomial function of the corrected air data, $$P_s(n, c, v, E) = \sum_{k=1}^{K} a_k(n, c, E) P_a^k(n, c, v) \qquad (1.4)$$

where $a_k$(n,c,E) is the energy dependent $k^{th}$ serial coefficient for each detector element (n,c) with the polynomial degree K. It is noted that the above definition to decompose the air corrected data into M sets of energy dependent serial projection data only requires a CT system to acquire the raw data at a single X-ray energy, for example at 120 kV, and there is no requirement for acquiring the raw data at multiple X-ray energies.

In an alternative embodiment of the present disclosure, the raw data 212 comprise the data acquired at multiple X-ray energies, for example at 80 kV and at 140 kV, or sinusoidal change of the X-ray energy between 80 kV and 140 kV through data acquisition.

In accordance with one embodiment of the present disclosure, the raw domain processor 220 takes the synthesized raw data $R_s(n,c,v)$, the offset corrected data $R_o(n,c,v)$, the iterated projection data $P_i(n,c,v,E)$, the air corrected data $P_o(n,c,v)$, and the X-ray spectrum $S(E)$, to compute the gradient term $g_k(n,c,E)$ for updating the $k^{th}$ serial coefficient $a_k(n,c,E)$ for detector element (n,c) as follows, $$g_k(n, c, E) = \sum_v D(n, c, v) S(E) e^{-P_i(n,c,v,E)} P_a^k(n, c, v) \Delta E \qquad (1.5)$$

where $D(n,c,v)$ is the difference between the synthesized raw data and the offset corrected data as follows, $$D(n,c,v) = R_s(n,c,v) - R_o(n,c,v) \qquad (1.6)$$

The raw domain processor 220 updates the energy dependent $k^{th}$ coefficient $a_k(n,c,E)$ for detector element (n,c) as follows in each iteration, $$a_k^{(u+1)}(n,c,E) = a_k^{(u)}(n,c,E) + \Delta Q \cdot g_k(n,c,E) \qquad (1.7)$$

where u and u+1 are the iteration steps, and $\Delta Q$ is a pre-determined step size, which is also previously optimized and stored in raw domain processor 220. The update of the energy dependent $k^{th}$ coefficient $a_k(n,c,E)$ results in the updated serial projection data defined by Eq. (1.4) accordingly.

In accordance with one embodiment of the present disclosure, the projection domain processor 230 receives the serial projection data 222, comprising a set of M serial projection data, $P_s(n,c,v,E)$ for $E=E_0, E_0+\Delta E, \ldots, E_0+(M-1)\Delta E$, and directly passes them to the raw synthesizer 250 without processing, i.e.

$$P_i(n,c,v,E) = P_s(n,c,v,E) \qquad (1.8)$$

In another embodiment of the present disclosure, the projection domain processor 230 takes the serial projection data 222, and performs a set of data-dependent processing steps including but not limited to such as scatter correction and destreaking to generate the iterated projection data 234.

In accordance with one embodiment of the present disclosure, the projection domain processor 230 takes the serial projection data 222 and the synthesized projection data 262, and generates the serial image data 232, denoted as $I_s(x,y,z,E)$, where x, y, z are the indices of the image pixels, where $x=0, \ldots, X-1, y=0, \ldots, Y-1, z=0, \ldots, Z-1$, and X, Y, and Z present the 3D CT image size at each dimension.

In accordance with one embodiment of the present disclosure, the serial image data 232 is generated iteratively by minimizing the following cost function $J(\hat{I}_s(E))$, comprising two terms: a data fidelity term and a regularization term, $$I_s(E) = \arg \min_{\hat{I}_s(E)} \underbrace{\left\| A\hat{I}_s(E) - P_s(E) \right\|_2^2}_{\text{data fidelity term}} + \underbrace{f(\hat{I}_s(E))}_{\text{regularization term}} \qquad (1.9)$$

$$\underbrace{\phantom{xxxxxxxxxxxxxxxxxxxxxxxxxx}}_{J(\hat{I}_s(E))}$$

where $I_s(E)$ is a column vector representation of the serial image data 232, also denoted as $I_s(x,y,z,E)$, A is the system model matrix relating the serial projection data 222 and the serial image data 232, $P_s(E)$ is a column vector representation of the serial projection data 222, also denoted as $P_s(n,c,v,E)$, $\hat{I}_s(E)$ is a column vector representation of the iterated image data 242, denoted as $\hat{I}_s(x,y,z,E)$, and $f(\cdot)$ is a regularization function regularizing the variable $\hat{I}_s(E)$, thus giving additional constraints for the optimization. The examples of such regularization functions are as in the form of p-norm as follows, $$f(x) = \|x\|_p^p \qquad (1.10)$$

where p is a pre-determined constant. In the case of p=1, the regularization problem is also called total variation regularization or L1 regularization; when p=2, the regularization problem is also called as L2 regularization. In the above iterative minimization process, the calculation of synthesized project data 262, $P_y(E) = A\hat{I}_s(E)$, is carried out by the projection synthesizer 260, and the synthesized projection data 262 is also denoted as $P_y(n,c,v,E)$.

In accordance with one embodiment of the present disclosure, the image domain processor 240 receives the serial image data 232 directly pass them to the projection synthesizer 260 without processing, i.e.

$$\hat{I}_s(x,y,z,E) = I_s(x,y,z,E) \qquad (1.11)$$

In an alternative embodiment of the present disclosure, the image domain processor 240 receives the serial image data 232, and performs a suite of image-based processing steps including but not limited to such as ring artifact removal, bone artifact correction, metal artifact reduction, and high-pass filtering to generate the iterated image data 242.

In accordance with one embodiment of the present disclosure, the image domain processor 240 generates the CT images 270, denoted as $I_{ct}(x,y,z)$, $$I_{ct}(x, y, z) = \sum_E b(E) I_s(x, y, z, E) \qquad (1.12)$$

where $b(E)$ is an energy dependent weighting coefficient for $E=E_0, E_0+\Delta E, \ldots, E_0+(M-1) \Delta E$, where $\Sigma_E b(E)=1$, resulting the generated CT images 270 being the weighted average of the serial image data 232.

While this disclosure has been particularly shown and described with references to the embodiments thereof, it will be understood by those skilled in the art that various changes in forms and details may be made therein without departing from the spirit and scope of the disclosure as defined by the following claims.

The invention claimed is:

1. A system for reconstructing CT images comprising:
   A. A CT data acquisition system for generating raw data for each detector element at each view;
   B. A raw domain processor for generating M sets of serial projection data for each detector at each view; wherein M is a predetermined number of bins of a discretized X-ray spectrum of the X-ray source corresponding to said CT data acquisition system;
   C. A projection domain processor for generating M sets of serial image data; wherein said projection domain processor also generates iterated projection data;
   D. An image domain processor for generating CT images; wherein said image domain processor also generates iterated image data;

E. A raw synthesizer for generating synthesized raw data; and,

F. A projection synthesizer for generating synthesized projection data, wherein the input data of said projection domain processor comprises said serial projection data, said iterated image data, and said synthesized projection data; wherein the input data of said image domain processor comprises said serial image data; wherein the input data of said raw synthesizer comprises said iterated projection data; wherein the input data of said projection synthesizer comprises said iterated image data.

2. The system of claim 1, wherein said raw domain processor also generates air corrected data; wherein each of said M sets of serial projection data is a polynomial function of said air corrected data with K serial coefficients; wherein K is the degree of said polynomial function.

3. The system of claim 2, wherein said raw domain processor generates said serial coefficients iteratively by updating said serial coefficients with gradient terms at each iteration.

4. The system of claim 3, wherein said raw domain processor also generates offset corrected data and uses said synthesized raw data, said offset corrected data, said discretized X-ray spectrum, said air corrected data, and said iterated projection data to generate said gradient terms at each iteration.

5. The system of claim 1, wherein said projection domain processor generates said serial image data iteratively by minimizing a cost function comprising a data fidelity term with said synthetic projection data and said serial projection data.

6. The system of claim 5, wherein said cost function includes a regularization term on said iterated image data.

7. The system of claim 1, wherein said image domain processor uses M pre-determined energy dependent weighting coefficients to compute a weighted average of said serial image data as said CT images.

8. The system of claim 1, wherein said raw synthesizer generates said synthesized raw data, denoted as $R_s(n,c,v)$, using said iterated projection data, denoted as $P_i(n,c,v,E)$, according to $$R_s(n, c, v) = \sum_E S(E) e^{-P_i(n,c,v,E)} \Delta E,$$

wherein S(E) is said discretized X-ray spectrum, $E=E_0, E_0+\Delta E, \ldots, E_0+(M-1)\Delta E$ is said pre-determined M bins of X-ray energy, $E_0$ is the first energy bin, $\Delta E$ is the energy bin size, n and c are the row index and column index of each detector element respectively, and v is the index of each view.

* * * * *